(12) United States Patent
Palfy et al.

(10) Patent No.: US 6,834,509 B2
(45) Date of Patent: Dec. 28, 2004

(54) DEVICES AND METHODS FOR SENSING CONDENSATION CONDITIONS AND FOR PREVENTING AND REMOVING CONDENSATION FROM SURFACES

(76) Inventors: Valerie Palfy, P.O. Box 11, Paoli, PA (US) 19301; Don A. Skomsky, 554 Highland Rd., West Chester, PA (US) 19380

( * ) Notice: Subject to any disclaimer, the term of this patent is extended or adjusted under 35 U.S.C. 154(b) by 0 days.

(21) Appl. No.: 10/356,606

(22) Filed: Feb. 3, 2003

(65) Prior Publication Data

US 2004/0050072 A1 Mar. 18, 2004

Related U.S. Application Data

(63) Continuation-in-part of application No. PCT/US02/29422, filed on Sep. 18, 2002, which is a continuation of application No. 09/953,891, filed on Sep. 18, 2001, now Pat. No. 6,470,696.

(51) Int. Cl.[7] ............................ F25D 21/02; F25B 21/02
(52) U.S. Cl. ............................... 62/140; 62/150; 62/3.4
(58) Field of Search ............................ 62/140, 36, 239, 62/150, 272; 15/250.05; 219/203, 507, 508, 509, 494, 497; 236/910; 165/202, 222, 223

(56) References Cited

U.S. PATENT DOCUMENTS

| | | | | |
|---|---|---|---|---|
| 3,934,111 A | * | 1/1976 | Roselli et al. | 219/203 |
| 4,109,562 A | | 8/1978 | MacDonald | 98/2.19 |
| 4,189,094 A | * | 2/1980 | Robinson | 236/46 R |
| 4,386,336 A | | 5/1983 | Kinomoto et al. | |
| 4,473,813 A | | 9/1984 | Kinjo et al. | |
| 4,580,354 A | * | 4/1986 | Lindberg | 34/486 |

(List continued on next page.)

OTHER PUBLICATIONS

Arnott, Ann; "The New High–Tech Gizmos"; Parade Magazine, 2001, p. 10.
Delphi Automotive Systems; "A Change in the Air: Intellek™ Humidity Sensor"; http://www.delphiauto.com/news/solutions/monthly/ms420–03012001; 2001.
Iowa State Energy Center; "Input Devices and Sensors : Analog Devices"; http://www.energy.iastate.edu/DDC_on-line/i%20o/chapter2io2.htm, pp. 6–8.
Linear Technology; "Choosing a Humidity Sensor"; Jul. 2001; wysiwyg://main.4/http://www.sensorsmag.com/articles/0701/54/main.shtml.
Panametrics; "MiniCAP 2—Relative Humidity Sensor"; Feb. 2001.
Sensirion; "SHTx/SHT7x Humdity & Temperature Sensmitter"; 2002.
Sensorsmag; "Sensors Wish List"; www.sensormag.com; May 2001.

(List continued on next page.)

Primary Examiner—Chen Wen Jiang
(74) Attorney, Agent, or Firm—Fish & Richardson P.C.

(57) ABSTRACT

A device and method is provided for sensing or predicting when condensation having a given physical state is present or imminent and for suppressing such condensation from a surface, such as a vehicle windscreen, eyewear, goggles, helmet visor, computer monitor screen, window, electronic equipment, etc, by preventing or removing it. A first thermal sensor is in thermally conductive contact with the surface. A second thermal sensor is in an environment separated from the surface. A humidity sensor is in the environment of the second thermal sensor. A circuit causes a condensation suppression mechanism to be activated for preventing or removing condensation having the given physical state from the surface when a temperature sensed by the first thermal sensor, a temperature sensed by the second thermal sensor, and a humidity sensed by the humidity sensor indicate that a condensation condition is either present or imminent and requires prevention or removal at the surface.

48 Claims, 12 Drawing Sheets

U.S. PATENT DOCUMENTS

| | | | | |
|---|---|---|---|---|
| 4,586,342 A | | 5/1986 | Morishita et al. | 62/3 |
| 4,693,172 A | * | 9/1987 | Harvey | 454/75 |
| 4,701,052 A | | 10/1987 | Schoen, Jr. | 356/369 |
| 4,915,715 A | | 4/1990 | Oshima et al. | 55/208 |
| 5,473,933 A | | 12/1995 | Soga et al. | |
| 5,511,417 A | * | 4/1996 | Paukkunen | 73/335.03 |
| 5,546,802 A | | 8/1996 | Yoshimura et al. | |
| 5,575,835 A | | 11/1996 | Bailey et al. | 96/7 |
| 5,653,904 A | | 8/1997 | Adlparvar et al. | 219/203 |
| 5,665,146 A | | 9/1997 | Mizobe | 96/7 |
| 5,801,307 A | | 9/1998 | Netzer | 73/170.17 |
| 5,809,826 A | | 9/1998 | Baker, Jr. | 73/75 |
| 5,814,726 A | * | 9/1998 | Mitter | 73/335.04 |
| 6,049,069 A | | 4/2000 | Hochstein | 219/497 |
| 6,101,815 A | | 8/2000 | van Oort et al. | 62/3.4 |
| 6,112,807 A | | 9/2000 | Dage | 165/202 |
| 6,205,805 B1 | | 3/2001 | Takahashi et al. | 62/271 |
| 6,207,967 B1 | | 3/2001 | Hochstein | 250/574 |
| 6,213,198 B1 | | 4/2001 | Shikata et al. | 165/202 |
| 6,230,501 B1 | | 5/2001 | Bailey, Sr. et al. | 62/51.1 |
| 6,422,062 B1 | * | 7/2002 | King et al. | 73/29.01 |
| 6,470,696 B1 | | 10/2002 | Palfy et al. | 62/140 |
| 6,508,408 B2 | | 1/2003 | Kelly et al. | |

OTHER PUBLICATIONS

Visteon Corporation; "Automotive OE"; http://www.visteon.com/technology/automotive/cli_autodefog.html; 2001.

Xentaur; "High Capacitance, Quasi–Linear Response"; Jul. 2001, http://www.xentaur.com/HiCap.htm.

Xentuar; "Hyper–Thin–Film (HTF) $Al_2O_3$ Sensors"; Jul. 2001, http://www.xentaur.com/Hprthin.htm.

* cited by examiner

OPTION 1

OPTION 2

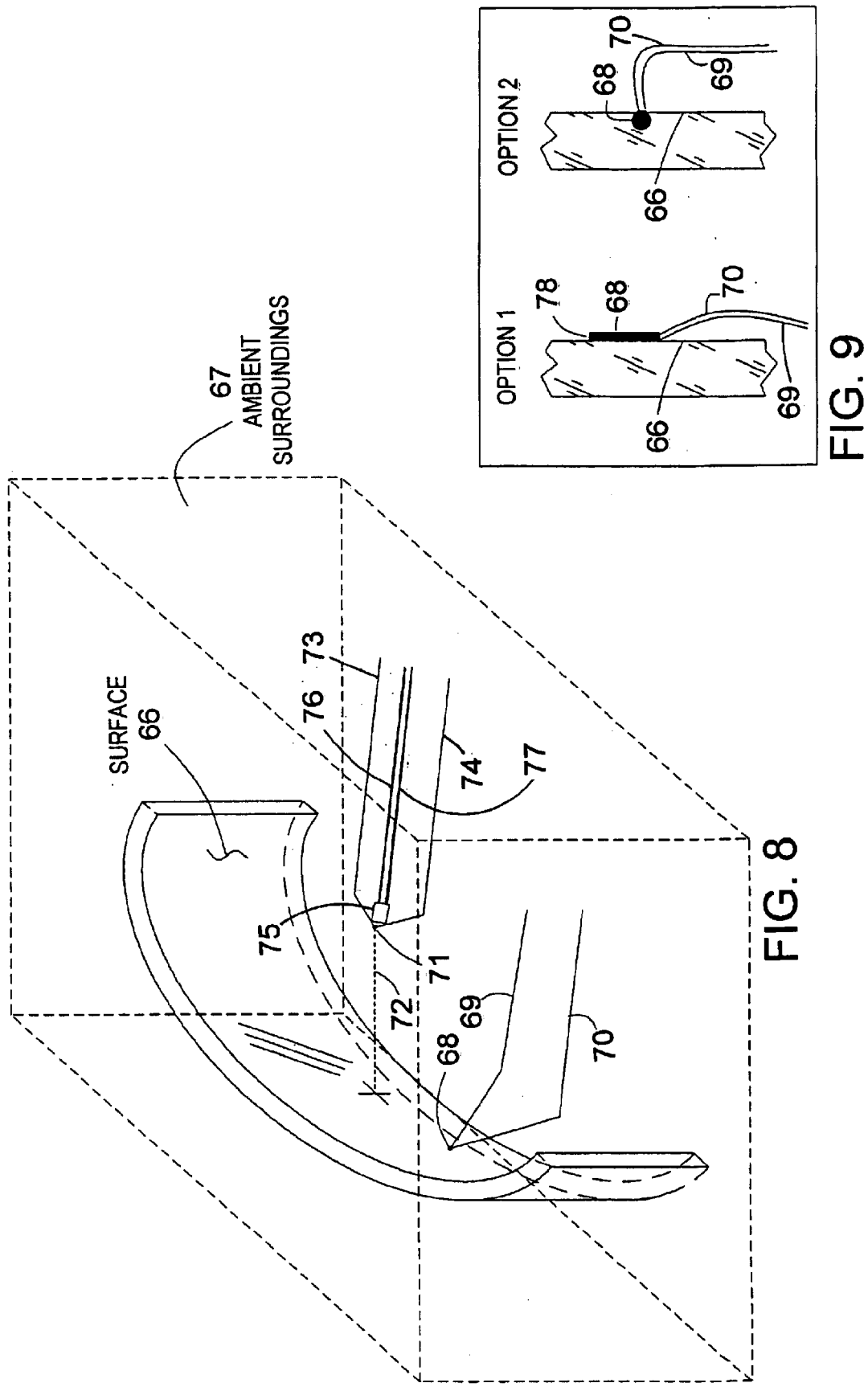

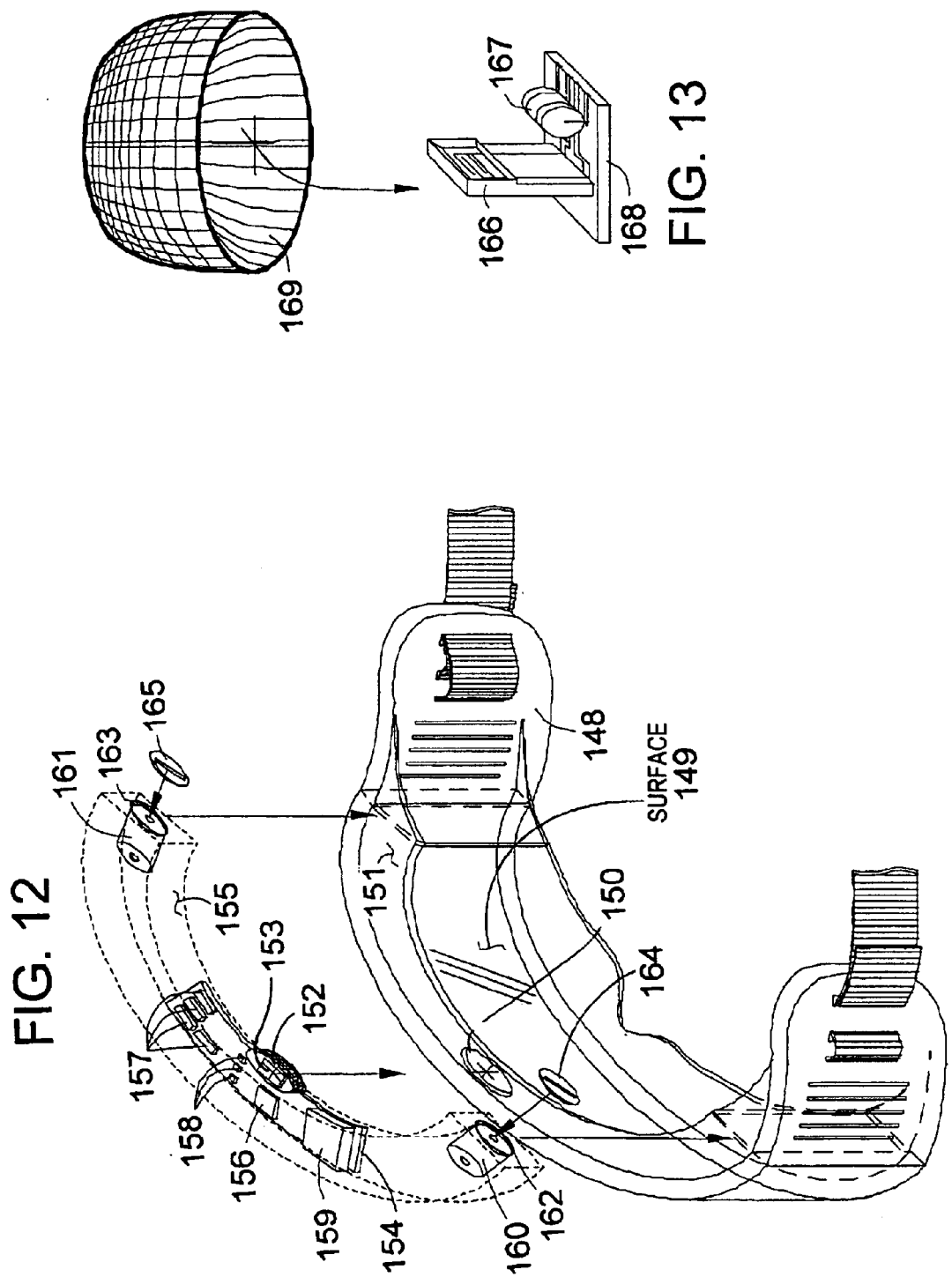

US 6,834,509 B2

DEVICES AND METHODS FOR SENSING CONDENSATION CONDITIONS AND FOR PREVENTING AND REMOVING CONDENSATION FROM SURFACES

CROSS-REFERENCE TO RELATED APPLICATIONS

This is a continuation-in-part application of Patent Cooperation Treaty application PCT/US02/29422, filed Sep. 18, 2002, the entire disclosure of which is hereby incorporated herein by reference, which is a continuation of U.S. application Ser. No. 09/953,891, filed on Sep. 18, 2001, now U.S. Pat. No. 6,470,696, the entire disclosure of which is hereby incorporated herein by reference.

TECHNICAL FIELD

The present invention relates to devices and methods for sensing condensation conditions and for preventing or removing such condensation from surfaces such as vehicle windscreens, eyewear, goggles, helmet visors, computer monitor screen, windows, electronic equipment, etc., and especially devices and methods that use a thermal sensor and a humidity sensor in an adjacent ambient space with respect to the surface, or in thermally conductive contact with a thermoelectric cooler (TEC), for automatically and dynamically sensing condensation conditions when condensation appears on a surface or before such condensation actually appears on a surface.

BACKGROUND

The level of moisture in air at any time is commonly referred to as relative humidity. Percent relative humidity is the ratio of the actual partial pressure of steam in the air to the saturation pressure of steam at the same temperature. If the actual partial pressure of steam in the air equals the saturation pressure at any given temperature, the relative humidity is 100 percent. If the actual partial pressure is half that of the saturation pressure, the relative humidity is 50 percent, and so forth.

Dew point temperature, also known as condensation temperature or saturation temperature, is a function of the level of moisture or steam that is present in the air, and is the temperature at which air has a relative humidity of 100 percent. Condensation of moisture on a surface occurs when the temperature of that surface is at or below the dew point temperature of air surrounding the surface.

When air having a relatively high content of moisture comes into contact with a surface having a temperature at or below the dew point temperature, steam will begin to condense out of the air and deposit as water droplets onto the surface. At this time, a thin layer of liquid water comprised of small water droplets forms on the surface, creating a visual hindrance or "fog" to an observer looking at or through the surface. Once, formed, the condensation can be dispersed and removed either by raising the temperature of the surface, thereby changing the water into steam, or by lowering the relative humidity of the air surrounding the surface, thereby allowing the droplets to evaporate.

Steam, as a gas, exists in a saturated state at pressures and corresponding temperatures that are predictable and measurable. Notably, the standard for steam's thermodynamic properties, including saturation pressures and temperatures, in the United States and arguably the world, is the ASME (American Society of Mechanical Engineers) Steam Tables. These thermodynamic property tables are readily obtainable from ASME, as well as from engineering texts.

In that steam possesses certain characteristics and traits as a saturated gas that are measurable and exact, equations have been developed that permit the engineer to approximate and predict the properties of steam at a desired set of conditions when its properties are known at a different, or datum, set of conditions. Such an equation, in the case of gas saturation pressures and temperatures, is entitled the Clausius-Clapeyron Equation. This equation, which may be described in several variations, may be best stated for the purposes at hand in the following form:

$$\ln\left[\frac{P_2^{sat}}{P_1^{sat}}\right] = \frac{\Delta H}{R} * \left(\frac{1}{T_1} - \frac{1}{T_2}\right)$$

where $P_1^{sat}$ is the saturation partial pressure at state 1, in units of psia;

$P_2^{sat}$ is the saturation partial pressure at state 2, in units of psia;

$\Delta H$ is the heat of vaporization, equal to approximately 755,087.46 (ft–lbf)/lbm for steam;

R is the gas constant, equal to approximately 85.8 (ft–lbf)/(lbm–° R) for steam;

$T_1$ is the temperature at state 1, in units of degrees Rankine; and $T_2$ is the temperature at state 2, in units of degrees Rankine.

Thus, using the Clausius-Clapeyron Equation, once steam's saturation pressure and temperature are known (the saturation pressure and temperature defining state 1 of the steam), given any other desired temperature, the saturation pressure at this temperature can be calculated to a high degree of accuracy (the temperature and calculated saturation pressure defining state 2 of the steam). Conversely, given any known state 1 conditions, for any desired saturated gas pressure, the saturation temperature can be calculated (the saturation pressure and calculated temperature defining state 2 of the steam).

SUMMARY

The invention provides a device and method for sensing or predicting when condensation is present or imminent and for suppressing such condensation from a surface by preventing it or removing it. A first thermal sensor is in thermally conductive contact with the surface. A second thermal sensor is in an environment separated from the surface. A humidity sensor is in the environment of the second thermal sensor. A circuit causes a condensation suppression mechanism to be activated for preventing or removing condensation having the given physical state from the surface when a temperature sensed by the first thermal sensor, a temperature sensed by the second thermal sensor, and a humidity sensed by the humidity sensor indicate that a condensation condition is either present or likely and requires prevention or removal at the surface. As used herein and in the claims, the term "suppress" encompasses prevention or preclusion of condensation conditions as well as, in the alternative, removal of existing condensation conditions.

The invention provides a convenient and practical mechanism for detecting condensation conditions quickly, before they manifest themselves on the surface. In certain embodiments the condensation suppression mechanism can be activated automatically when a condensation condition is detected, thereby providing convenience and safety where the surface is a windscreen of a vehicle, for example, or goggles, a helmet visor, computer monitor screen, window, electronic equipment enclosure.

In one embodiment of the invention, the second thermal sensor is in thermally conductive contact with a cooling device, and a circuit activates the cooling device in order to maintain the second thermal sensor at a temperature that is lower than a temperature of the first thermal sensor. The humidity sensor is in thermally conductive contact with the cooling device. The circuit causes the condensation suppression mechanism to be activated when the humidity sensor indicates a presence of high humidity conditions or condensation at the temperature that is lower than the temperature of the first thermal sensor.

In alternative embodiments of the invention, the environment of the second thermal sensor is in an adjacent ambient space with respect to the surface. The circuit determines that the condensation condition requires suppression at the surface by determining, from the temperature sensed by the second thermal sensor and the humidity sensed by the humidity sensor, the pressure of steam in the environment of the second thermal sensor. Then, the circuit may either determine a ratio of the pressure of steam in the environment of the second thermal sensor to the saturated steam pressure at the temperature sensed by the first thermal sensor, or determine a difference between a temperature sensed by the first thermal sensor and a dew point temperature associated with the pressure of steam in the environment of the second thermal sensor.

Thus, in certain embodiments of the invention, instead of measuring RH at an intentionally lowered temperature relative to the surface in question, RH (and temperature) can be measured in the surrounding ambient air adjacent to and in the proximity of the surface itself. Through calculation, the measurements taken in the surrounding ambient air can be extrapolated using the Clausius-Clapeyron Equation or any of its derivatives to determine whether condensation conditions exist on the surface in question or are imminent. Thus, it is not necessary physically to create a simulated (state 2) temperature in which a (state 2) relative humidity (RH) value can be measured.

Numerous additional features, objects, and advantages of the invention will become apparent from the following detailed description, drawings, and claims.

DESCRIPTION OF DRAWINGS

FIG. 8 is a diagram of a surface in combination with a pair of thermal sensors and a humidity sensor in accordance with another embodiment of the invention FIG. 9 is a cross-sectional drawing of two options for incorporating a thermal sensor into a surface.

FIG. 12 is a drawing of a condensation detection and suppression system, in accordance the invention, applied to a pair of goggles.

FIG. 13 is an exploded view of a portion of the electronic circuitry sensors juxtaposed relative to their protective hydrophobic cover as embodied in FIG. 12.

Like reference symbols in the various drawings indicate like elements.

DETAILED DESCRIPTION

Figure 1:
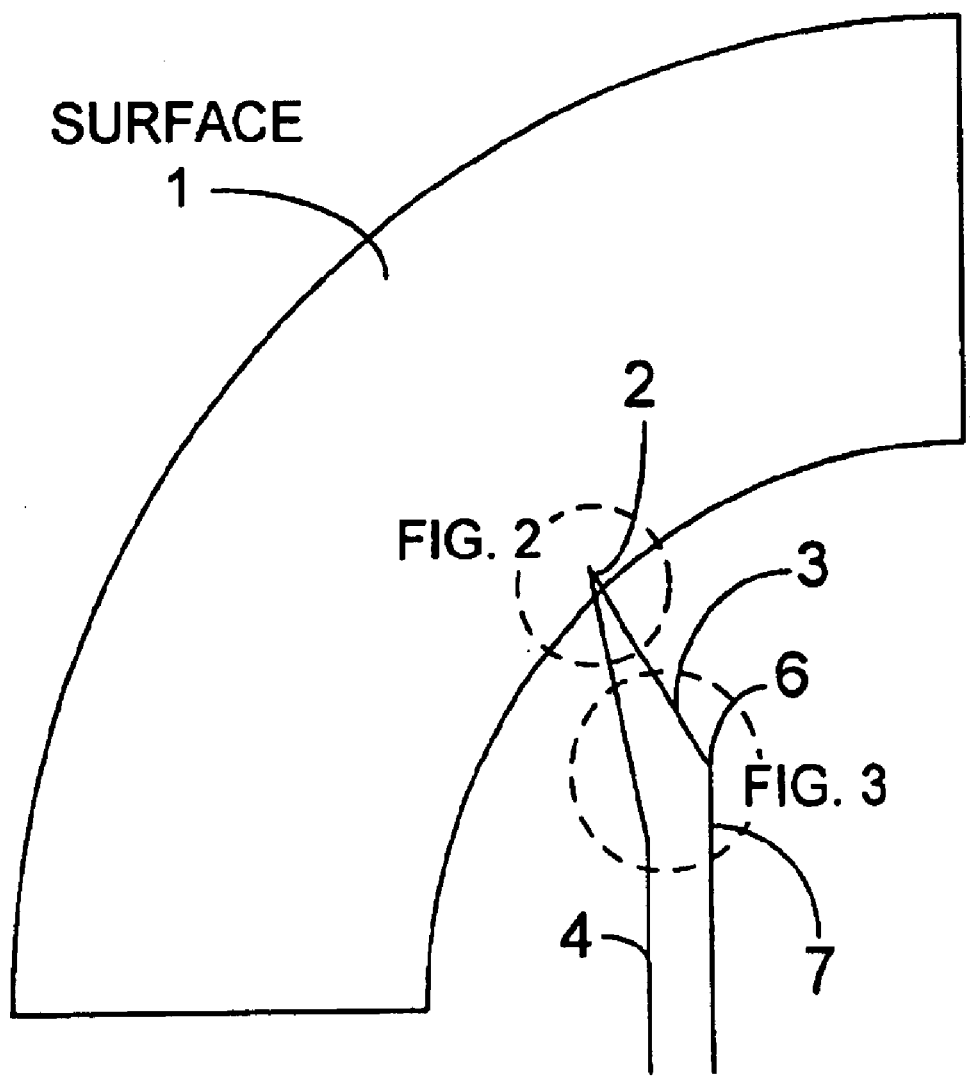
FIG. 1 is a diagram of a surface in combination with a pair of thermal sensors in accordance with the invention.

With reference to FIG. 1, an automatic sensing and condensation prevention and removal system according to the invention includes two thermal sensors 2 and 6. Thermal sensor 2 is mechanically affixed to or embedded within a surface 1 from which condensation conditions are to be sensed and/or condensation is to be removed, such as a windscreen, goggles, a visor for a military helmet, pilot helmet, space-suit helmet, or other type of helmet, a computer monitor screen (such as a screen for a commercial electron beam or LCD computer monitor placed outdoors or in a high-humidity environment, such as in an industrial panel), a window or other transparent or translucent pane or enclosure (such as common windows in office buildings or enclosures that may house documents or other sensitive materials such as artwork and artifacts in museums or historic works), including plastics, an electronic equipment enclosure (such as a transparent or non-transparent enclosure for computer equipment, telecommunications equipment, etc. that might be placed outdoors or in high-humidity environments in which condensation might appear on the inside surface of the enclosure).

Each of the thermal sensors is a thermocouple formed by the thermal fusion of two dissimilar but electrically insulated metal conductors. In particular, the thermal fusion of metal conductors 3 and 4 forms thermal sensor 2 and the thermal fusion of metal conductors 3 and 7 forms thermal sensor 6. Conductors 4 and 7 are of the same electro-conductive material and are of the same length.

If the temperatures of the bodies sensed by thermal sensors 2 and 6 are exactly the same, the thermocouple circuit through conductors 4 and 7 creates no electrical current. If the temperatures are not identical, a current is generated through this thermocouple circuit through conductors 4 and 7, this current being proportional to the temperature difference of the two thermocouple junctions, as was first discovered by Thomas Seebeck in 1821.

The integrated sensing and condensation prevention and removal device creates an intentional temperature difference between thermocouples 2 and 6 by the thermoelectric cooling effect of a thermoelectric cooler (TEC) onto which thermocouple 6 is mechanically affixed.

Figure 2A:
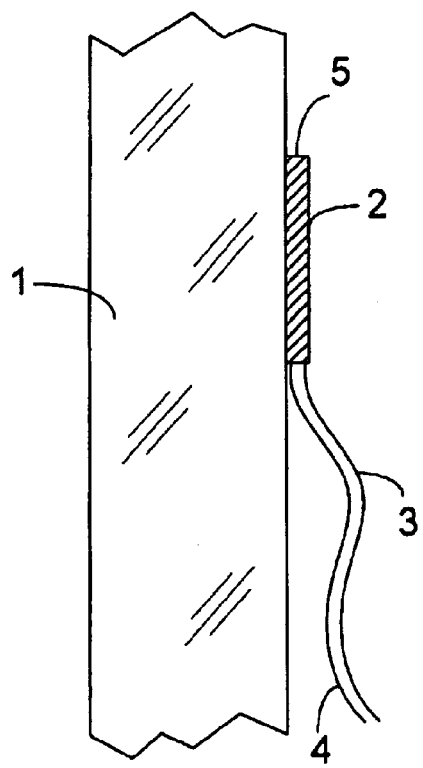
FIG. 2 is a cross-sectional drawing of two options for incorporating a thermal sensor into a surface.
Figure 2B:
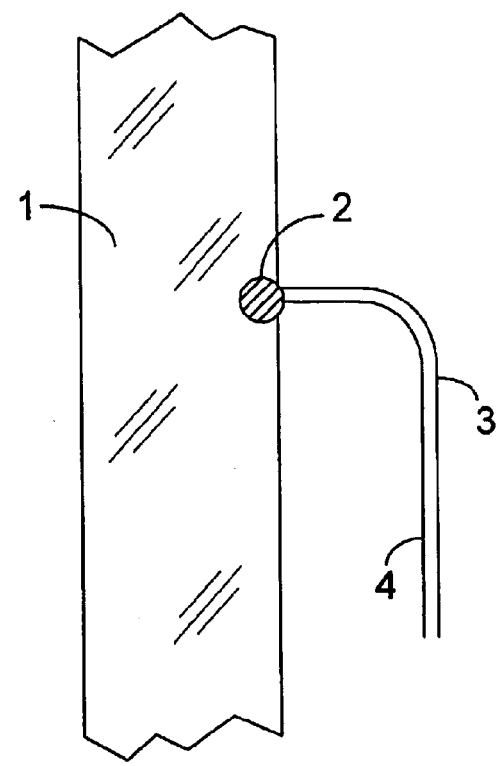

With reference to FIG. 2, thermal sensor 2 may be mechanically affixed to surface 1 by an adhesive 5 (Option 1), or thermal sensor 2 may be embedded within surface 1 (Option 2).

Figure 3:
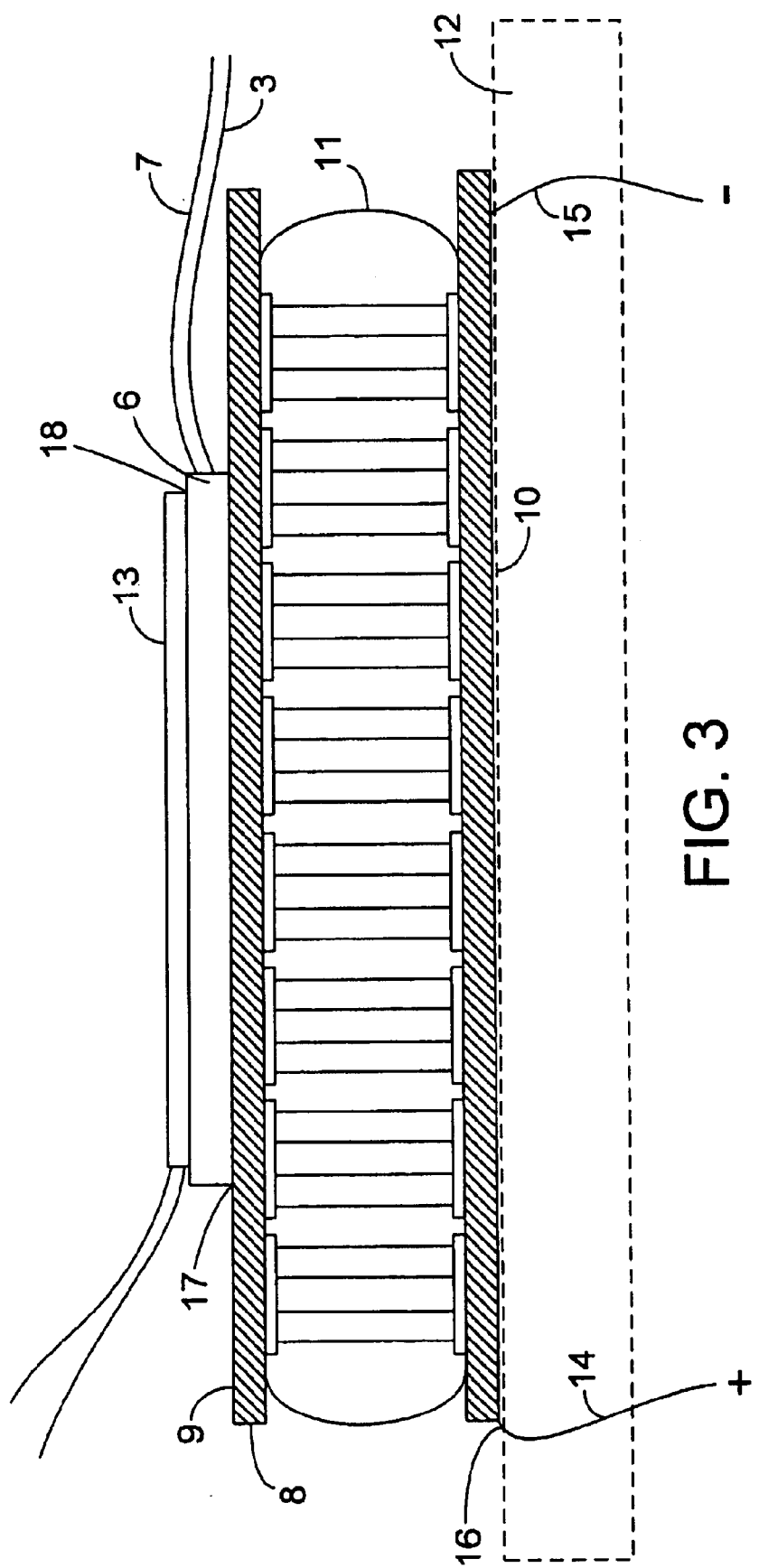
FIG. 3 is a cross-sectional drawing of thermoelectric cooler according to the invention in combination with a thermal sensor.
Figure 6:
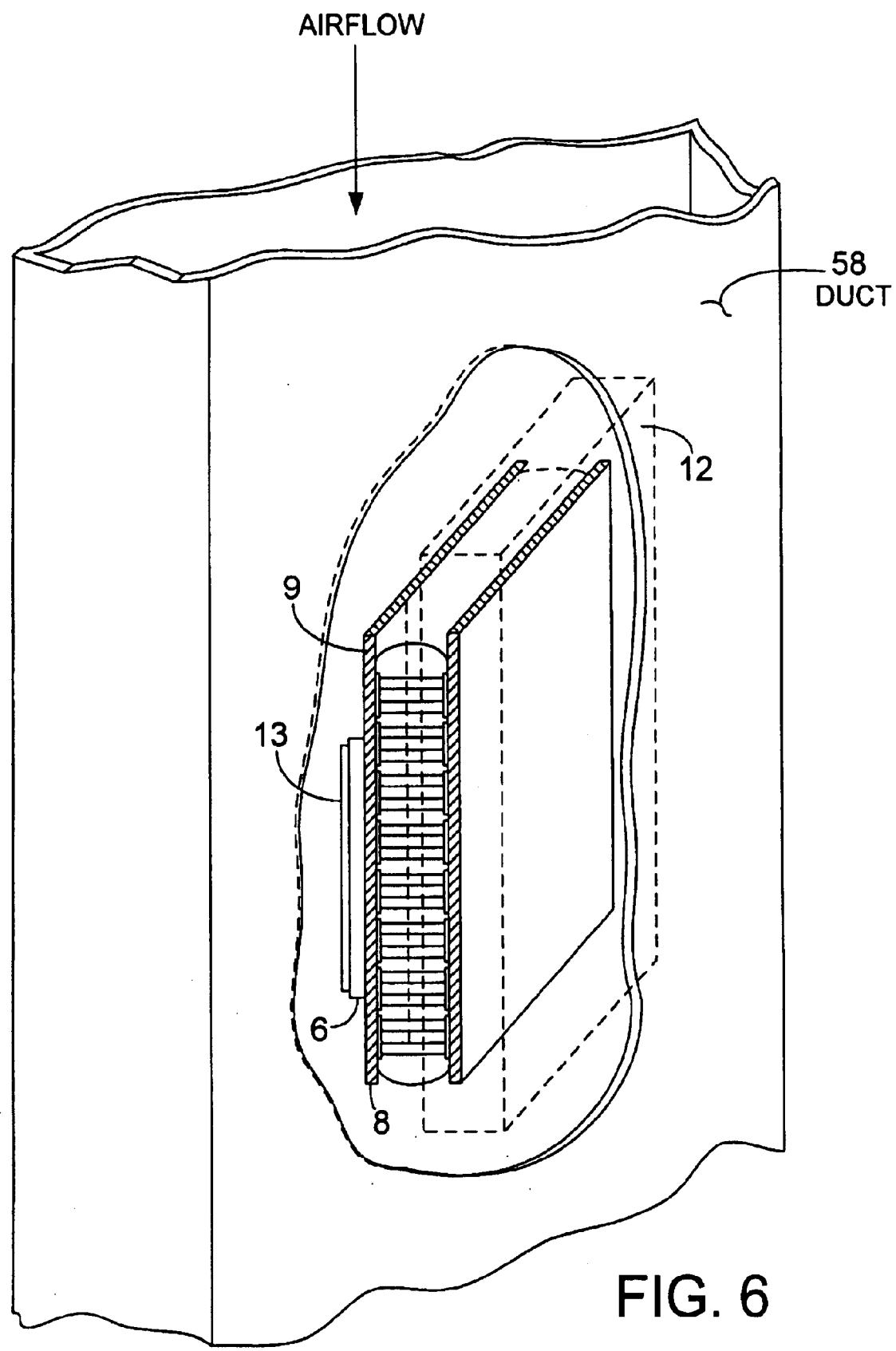
FIG. 6 is a drawing of the thermoelectric cooler and thermal sensor of FIG. 3 within an air duct, the air duct being shown in partial cut-away view.

With reference to FIG. 3, thermal sensor 6 is mechanically affixed by means of an adhesive 17 to the exterior face of the cold junction side 9 of thermoelectric cooler (TEC) 8. The exterior face of the hot side 10 of TEC 8 may be mechanically bonded or otherwise attached to an optional heat sink 12. A humidity sensor 13, illustrated as a thin-film capacitive sensor but which may be any other sensing device that performs a similar function, is bonded by a mechanical bond 18 to thermocouple 6. Thus, TEC cold-side face 9, thermocouple 6, and capacitive sensor 13 will always be at the same temperature. With reference to FIG. 6, TEC 8, thermal sensor 6, and thin-film capacitive sensor 13 are placed within the recirculation or outside air duct 58, with heat sink 12 being attached to air duct 58.

Figure 4:
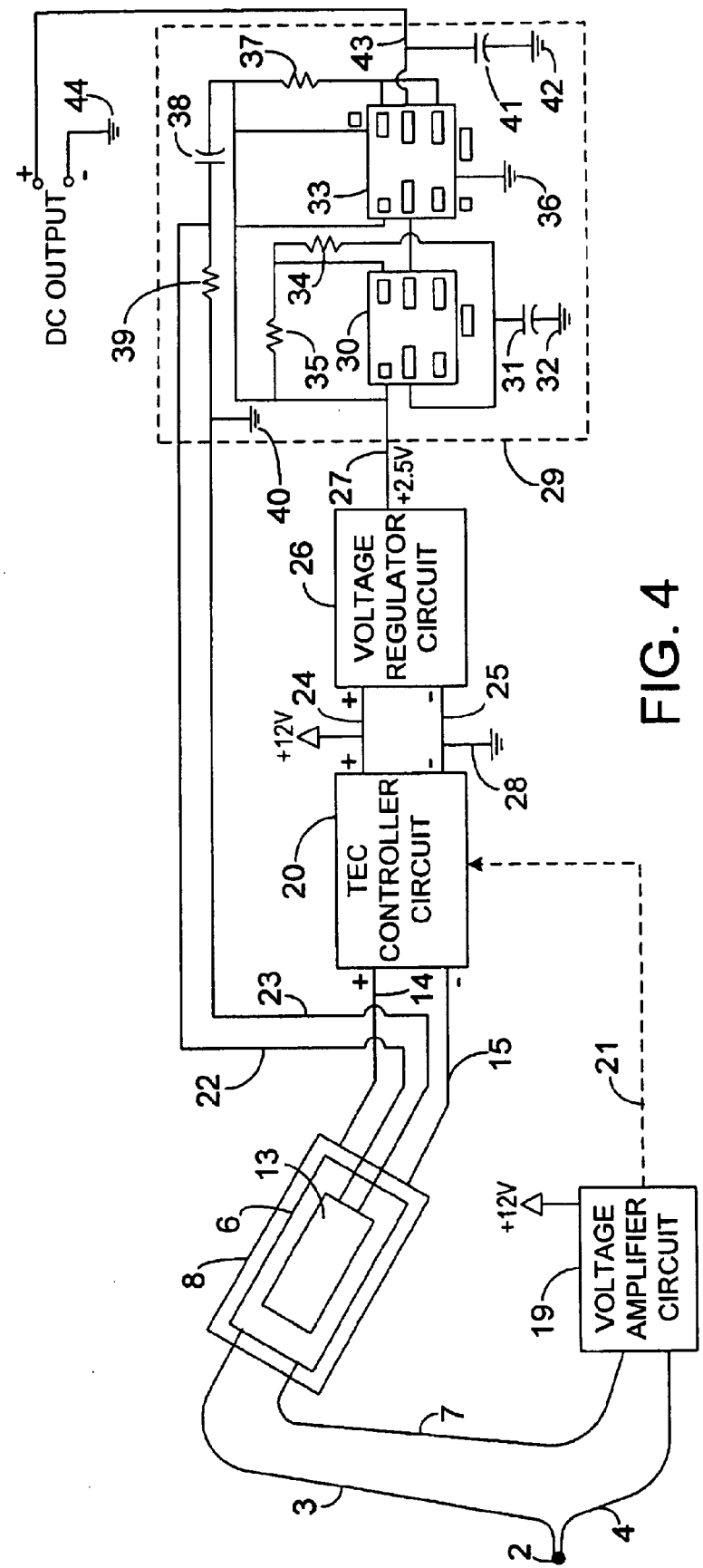
FIG. 4 is a block diagram of the electrical circuitry for an automatic sensing system according to the invention.

With reference to FIG. 4, as the above-mentioned intentionally-created temperature difference is created between thermocouples 2 and 6, and, consequentially, as current is developed within the thermocouple circuit, the resultant voltage difference across conductors 4 and 7 is measured and amplified by voltage amplifier circuit 19. This voltage signal is adjusted and offset for any impressed thermocouple effects due to any dissimilar metal junctions created by the connection of conductors 4 and 7 to voltage amplifier circuit 19 itself. The voltage signal is thereafter fed to TEC controller circuit 20, within which the signal is compared to a pre-established differential voltage set point. Thereafter, TEC controller circuit 20, supplied with an electrical power source and electrically grounded at ground 28, electrically modulates a voltage that is applied to TEC 8 by conductors 14 and 15, in order to maintain the cold face of TEC 8 at a temperature level that is a predetermined amount below the temperature of the windscreen, goggles, helmet visor, computer monitor screen, window, electronic equipment enclosure, or other surface.

The integrated sensing and condensation prevention and removal device is operated in a manner such that a constant difference is dynamically maintained between the temperature established at thermal sensor 6 by the action of TEC 8 and the temperature measured at the surface by thermal sensor 2. Therefore, regardless of the temperature of the surface, the temperature established at the cold-side face of TEC 8 onto which thermal sensor 6 is affixed will always be lower than that of the surface by a predetermined amount.

Ambient air or outside air flows over thin-film capacitive sensor 13. The capacitance of capacitive sensor 13 will be proportional to the relative humidity of the surrounding air. Because capacitive sensor 13 is maintained at a temperature less than that of the windscreen, goggles, helmet visor, computer monitor screen, window, electronic equipment enclosure, or other surface, the humidity level sensed will always be greater than that at the surface, and any liquid condensation will always form on capacitive sensor 13 before it forms on the surface.

Thin-film capacitive sensor 13 is connected by conductors 22 and 23 to capacitance-to-voltage circuit 29. Conductor 23 and capacitance-to-voltage circuit 29 are connected to a common electrical ground 40. Capacitance-to-voltage circuit 29 is supplied regulated 2.5-volt DC power by conductor 27 from voltage regulator circuit 26, which is in turn energized by an electrical power source and an electrical ground 28. Capacitance-to-voltage circuit 29 includes two #7556 timing integrated circuits 30 and 33, resistors 34, 35, 37, and 39, and filter capacitors 31, 38, and 41. Timing integrated circuits 30 and 33 are electrically grounded at junctions 32, 36, 42, and 44.

Capacitance-to-voltage circuit 29 transforms the constant 2.5-volt DC supply voltage into a high-frequency AC signal. Thin-film capacitive sensor 13 is integrated into capacitance-to-voltage circuit 29 in a manner such that any capacitance of capacitive sensor 13 is transformed into a positive DC voltage relative to ground 44, at conductor 43 of capacitance-to-voltage circuit 29. The capacitance of capacitive sensor 13 increases as humidity increases, thereby resulting in an increased voltage at conductor 43. The capacitance of capacitive sensor 13 is at a maximum when liquid moisture condenses onto capacitive sensor 13. This condensation of liquid moisture onto capacitive sensor 13, occurs when the temperature of capacitive sensor 13 is at or below the dew point of the ambient air.

Figure 5:
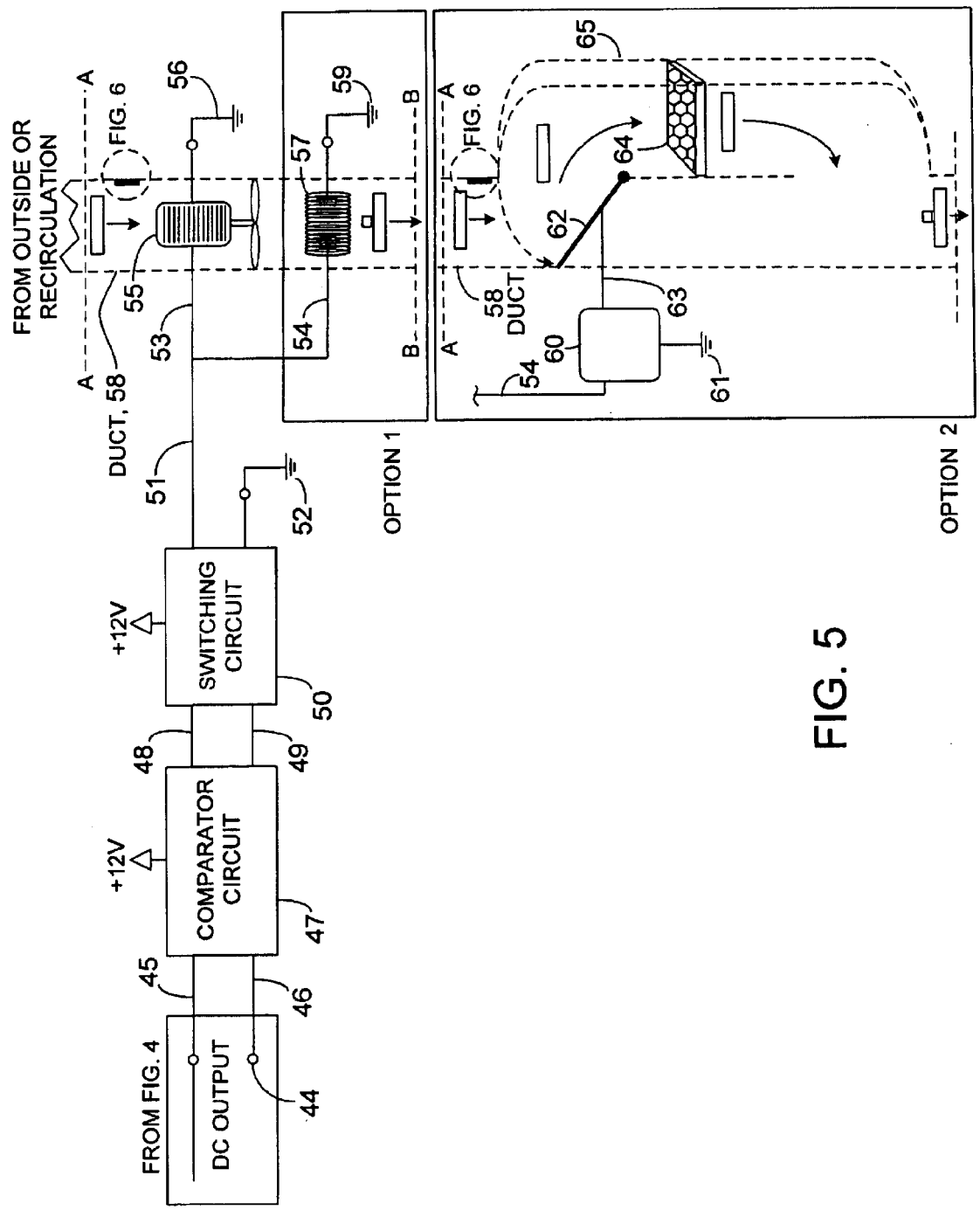
FIG. 5 is a block diagram of the electrical circuitry for two options of a condensation suppression system configured to be combined with the automatic sensing system of FIG. 4.

With reference to FIG. 5, the output signal of the capacitance-to-voltage circuit is connected by conductors 45 and 46 to comparator circuit 47. This output signal is compared to a set point voltage previously established in comparator circuit 47. If the signal is less than a pre-established set point, the signal is interpreted as meaning that fogging of the surface is not present or imminent. If the signal is equal to or greater to the pre-established set point, the signal is interpreted as meaning that fogging of the surface is present, imminent or likely to occur, in which case the system activates condensation suppression action.

If the signal from the capacitance-to-voltage circuit is equal to or greater than the pre-established set point, an electrical signal is directed to switching circuit 50 through conductors 48 and 49, thereby causing the internal electronic or mechanical contactors of switching circuit 50 to close. Thereafter, electrical power is directed from switching circuit 50 through conductor 51, which branches into conductors 53 and 54. Conductor 53 is connected to a single-speed or multiple-speed fan 55 located within duct 58. When fan 55 is energized, it rotates or increases its speed in order to generate or increase the volume of airflow directed toward the windscreen, goggles, computer monitor screen, window, electronic equipment enclosure, or other surface. The TEC, the thermal sensor mechanically bonded thereto, and the capacitive sensor are positioned within duct 58 upstream of fan 55.

FIG. 5 illustrates a first option (Option 1), according to which electrical power is applied by conductor 54 to electrical heating coil 57. Both fan 55 and heating coil 57 are electrically grounded by grounds 56 and 59 respectively. Energization of heating coil 57 raises the temperature of the air flowing over the heating coil element and thereafter flowing to and onto the face of the surface, thereby raising the temperature of the surface and the ambient space surrounding it so as to preclude condensation, or alternately if condensation is present, vaporizing water droplets deposited thereon.

According to a second option (Option 2), electrical power is applied by conductor 54 to an electric motor or solenoid actuator 60, which is electrically grounded by ground 61. Electric motor or solenoid actuator 60 is connected by linkage arm 63 to damper 62, which moves as indicated in FIG. 5 so as to divert the airstream to an adjacent but interconnecting and parallel duct 65 within which a heater core 64 is mounted. Heater core 64 raises the temperature of the airstream passing through parallel duct 65. Thereafter, the heated air is directed toward and onto the face of the surface, thereby raising the temperature of the surface and the ambient space surrounding it so as to preclude condensation, or alternately if condensation is present, vaporizing water droplets deposited thereon.

As a further option, the hot side face of the TEC may be used to provide heat, in lieu of the heating coil 57 or heater core 64, to the air flowing toward and onto the face of the surface, thereby precluding condensation, or alternatively if condensation is present, vaporizing water droplets deposited thereon.

As yet a further option, since there will not be any ductwork per se in a helmet or goggles, or within certain other equipment having surfaces to be defogged, fan 55, heating coil 57 and heater core 64 may be replaced by a heating coil embedded in or on the visor, etc., as micro-fine electro-resistive wires, or by an infrared source positioned so as to radiate onto the surface.

Figure 7:
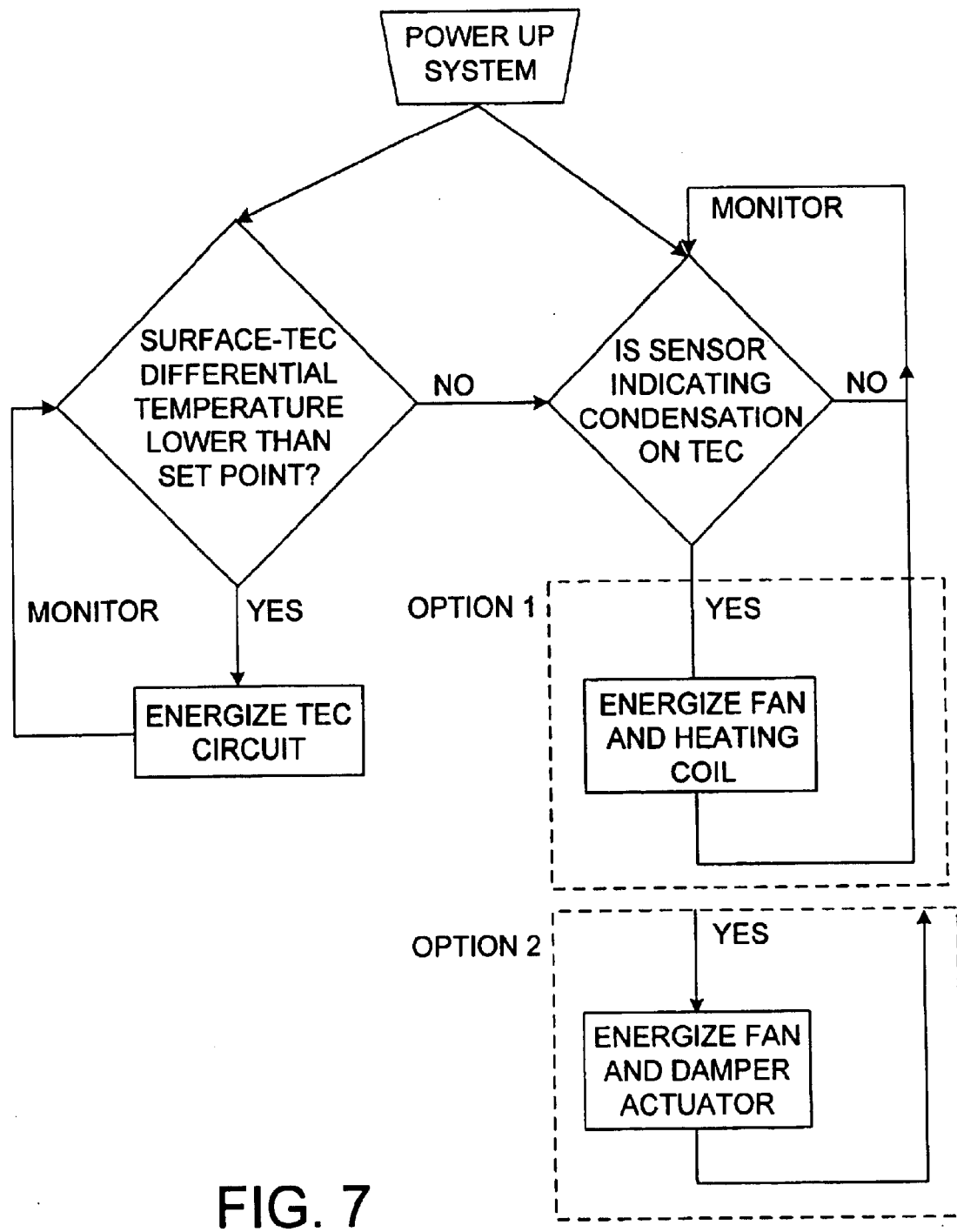
FIG. 7 is a flow diagram of a method for automatically sensing condensation conditions and for suppressing condensation from surfaces using the system illustrated in FIGS. 1–6.

With reference to FIG. 7, once the automatic sensing and condensation prevention and removal system is powered up, the difference in temperature between the windscreen, goggles, helmet visor, computer monitor screen, window, electronic equipment enclosure, or other surface and the TEC is monitored to determine whether it is lower than a pre-established set point, and the TEC is energized to the extent necessary-to raise the difference to the set point. Also, the capacitive sensor is monitored to determine whether it indicates the presence of condensation. If the capacitive sensor indicates the presence of condensation a fan is energized, and either a heating coil or a damper actuator is activated.

With reference to FIG. 8, an alternative embodiment of an automatic sensing and condensation preclusion and removal system according to the invention includes two thermal sensors 68 and 71. Thermal sensor 68 is mechanically affixed to or embedded within surface 66, for which condensation conditions are to be monitored and/or from which condensate liquid is to be removed. Surface 66 can be, for example, a windscreen for a vehicle, a visor for a military helmet, pilot helmet, space-suit helmet, or other type of helmet, a visor for safety or non-safety apparatus, goggles, glasses, or other type of visor or goggle, a full-face air purifying respirator mask, a self-contained breathing apparatus (SCBA) mask, or other type of respirator mask, a computer monitor screen (such as a screen for a commercial electron beam or LCD computer monitor placed outdoors, in a cool or cold environment or in a high-humidity environment, such as in an industrial panel), a window or other transparent or translucent pane or enclosure (such as common windows in office buildings or enclosures that may house documents or other sensitive materials such as artwork and artifacts in museums or historic works), including plastics, an electronic equipment enclosure (such as a transparent or non-transparent enclosure for computer equipment, telecommunication equipment, cameras, projection equipment, transmitters, receivers, transceivers, or like components or objects that may be placed outdoors or in cool or cold environments or in high-humidity environments in which condensation might appear), optical equipment such as telescopes, binoculars, instrument bezels, viewing windows, eyeglasses and prescription lenses, electronic circuitry and circuit boards, and like components.

As schematically shown, the sensors may each be a thermocouple, formed by the fusion of two dissimilar metal conductors, a resistance temperature detector (RTD), a thermistor, or any electronic thermal measurement device performing the same function. Thermal sensor 68 is electrically connected to conductors 69 and 70, while thermal sensor 71, positioned adjacent to and in close proximity to surface 66, at distance 72, in the ambient surroundings 67, is electrically connected to conductors 73 and 74. Additionally, a humidity sensor 75, illustrated as a thin-film capacitive relative humidity sensor, but which may be any other sensing device that performs a similar function is positioned immediately adjacent to thermal sensor 71, but also may be mechanically affixed to or otherwise mechanically attached to thermal sensor 71, it also being in close proximity to surface 66, at distance 72, in the ambient surroundings 67. Capacitive sensor 75 is electrically connected to conductors 76 and 77.

With reference to FIG. 9, thermal sensor 68 may be mechanically affixed to surface 66 by means of adhesive 78 (Option 1), or thermal sensor 68 may be imbedded within surface 66 (Option 2).

Figure 10:
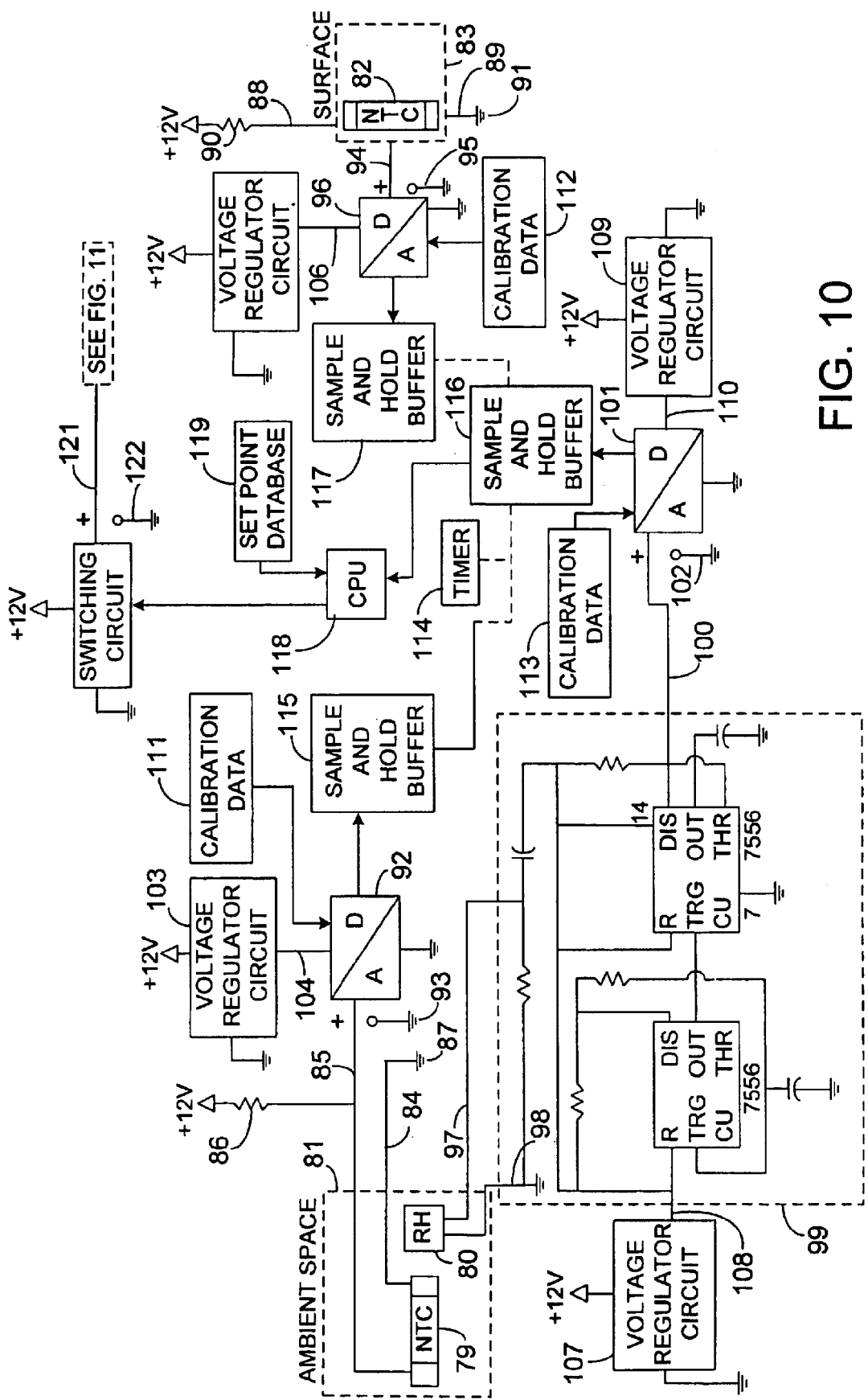
FIG. 10 is a block diagram of electrical circuitry for automatic sensing systems according to the invention of the type shown in FIG. 8.

With reference to FIG. 10, in one embodiment of the circuitry for a condensation detection and suppression system of the type shown in FIG. 8, thermal sensor 79, illustrated as a negative temperature coefficient (NTC) thermistor, but which may be any other temperature-sensing device that performs a similar function, is positioned within ambient space 81. Thin-film relative humidity sensor 80 is also positioned within the ambient space 81, in close proximity to thermal sensor 79. A second thermal sensor 82 is embedded within or affixed to surface 83. The first thermal sensor 79 is part of a voltage divider circuit, formed by a DC voltage source, resistor 86, conductors 84 and 85, and ground 87. Similarly, the second thermal sensor 82 is part of a second voltage divider circuit, formed by a DC voltage source of the same potential, resistor 90, conductors 88 and 89, and ground 91. As is illustrated in this embodiment, the resistance of each thermal sensor is proportional to the temperature of the material surrounding it. Thus, in the ambient space, the resistance of thermal sensor 79, and hence the voltage across thermal sensor 79, is proportional to the temperature of the air in the ambient space, resulting in a finite voltage input through conductor 84 to the analog-to-digital converter (ADC) 92 relative to ground 93. ADC 92 is supplied power through conductor 104 by voltage regulator circuit 103 that is connected to a DC power source.

Similarly, the resistance of thermal sensor 82, and hence the voltage across thermal sensor 82, is proportional to the temperature of surface 83, resulting in a finite voltage input to ADC 96 through conductor 94 relative to ground 95. ADC 96 is supplied power through conductor 106 by a voltage regulator circuit 105 that is connected to a DC power source.

Ambient air or outside air flows over thin-film capacitive sensor 80 in the ambient space 81. The capacitance of capacitive sensor 80 is proportional to the relative humidity of the surrounding air. Thin film capacitive sensor 80 is connected by conductors 97 and 98 to the capacitance-to-voltage circuit 99, the relative humidity level thus resulting in a finite voltage input to ADC 101 through conductor 100 relative to ground 102. The capacitance-to-voltage circuit 99 is supplied power through conductor 108 by a voltage regulator circuit 107 that is connected to a DC power source. ADC 101 is supplied power through conductor 110 by a voltage regulator circuit 109 that is connected to a DC power source.

Alternatively, a single voltage regulator connected to conductors 104, 106, and 110 and a single DC power source be may used instead of individual voltage regulators 103, 105 and 109.

The voltage level across ambient space thermal sensor 79 is converted in ADC 92 to a digital signal, thereafter being appropriately modified to account for any sensor error or non-linearity, as necessary, by calibration data 111. Similarly, the voltage level across surface thermal sensor 82 is converted in ADC 96 to a digital signal, thereafter being appropriately modified to account for any sensor error or non-linearity, as necessary, by calibration data 112. The voltage level across the output conductor 100 relative to ground 102 of the ambient space relative humidity sensor circuit 99 is converted in ADC 101 to a digital signal, thereafter being appropriately modified to account for any sensor error or nonlinearity, as necessary, by calibration data 113.

Internal timer 114 sets the period of data sampling (or data polling) for sample-and-hold buffers 115, 116, and 117, such that the acquisition of temperature and relative humidity data occurs concurrently. Each buffer may be configured to retain such data in flash memory or in a stack arrangement, such that the newest data replaces the data previously recorded. Subsequently, digital measurement data of ambient space temperature, surface temperature, and ambient space relative humidity are input to central processing unit (CPU) 118 for analysis. CPU 118, which retains a pre-programmed digital instruction set, accesses a set-point database 119 during computation to establish whether condensation preclusion or removal action is indicated. In such an event, CPU 118 initiates a signal-to-switching circuit 120, thereby causing internal electronic or mechanical contactors to close. Thereafter, DC electrical power relative to ground 122 is directed from switching circuit 120 through conductor 121 thus energizing components downstream.

Figure 11:
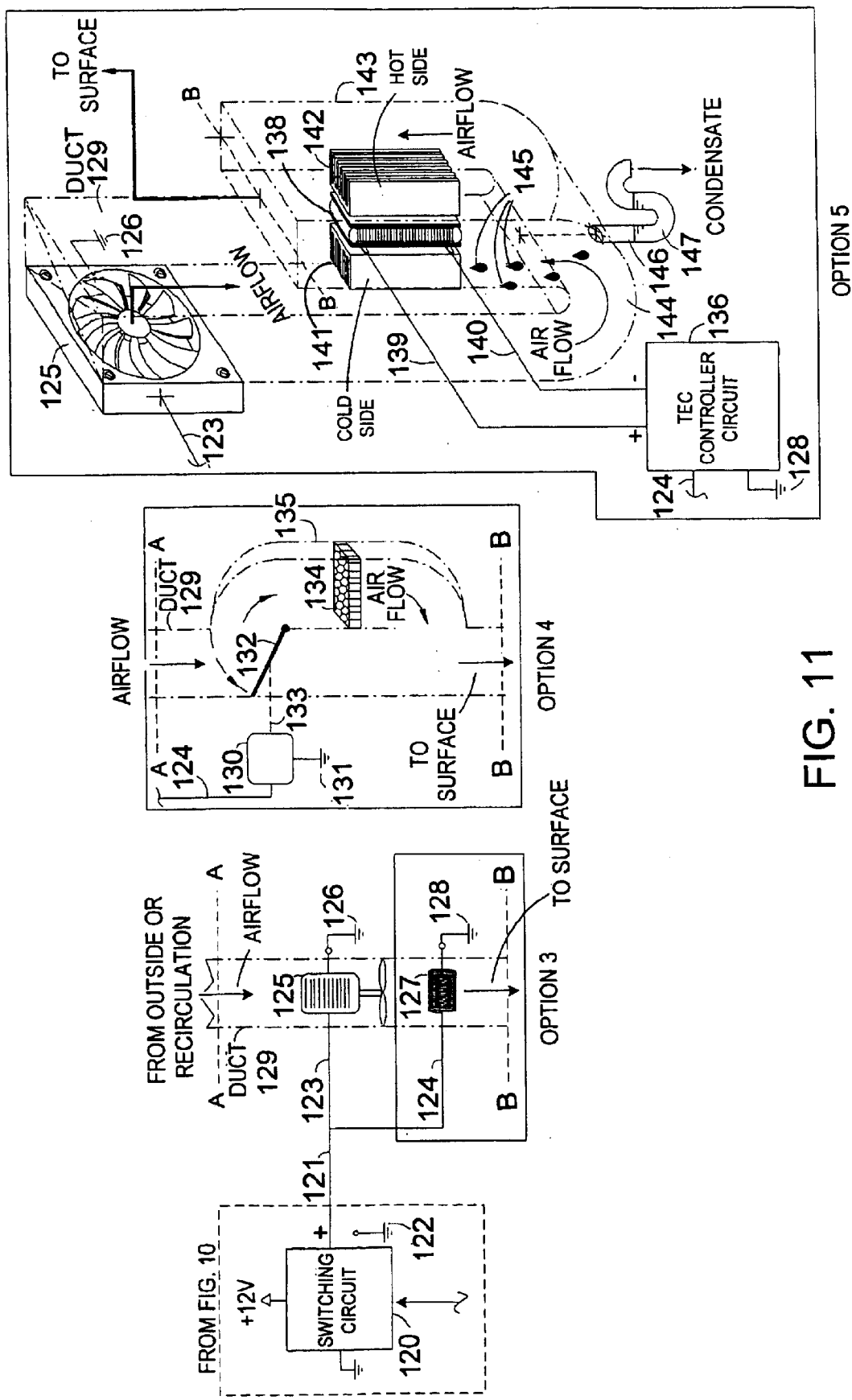
FIG. 11 is a block diagram of the electrical circuitry for three embodiments of a condensation suppression system configured to be combined with the automatic sensing system of FIG. 10.

With reference to FIG. 11, conductor 121 at the output of switching circuit 120 branches into two conductors 123 and 124. Conductor 123 is connected to a single-speed or multi-speed fan 125 located within duct 129. When fan 125 is energized, it rotates or increases its speed in order to generate or increase the volume of airflow directed toward the surface, thereby raising the temperature of the surface and the ambient space surrounding it so as to preclude condensation, or alternately if condensation is present, vaporizing water droplets deposited thereon.

FIG. 11 illustrates a further option (Option 3), according to which electrical power is applied by conductor 124 to electric heating coil 127. Both the fan and the heating coil are electrically grounded by grounds 126 and 128 respectively. Energization of heating coil 127 raises the temperature of the air flowing over the heating coil element and thereafter flowing to and onto the face of the surface, thereby raising its temperature and the ambient space surrounding it and precluding condensation, or alternatively if condensation is present, vaporizing water droplets deposited thereon.

According to a further option (Option 4), electrical power is supplied by conductor 124 to an electric motor or solenoid actuator 130, which is electrically grounded by ground 131. Electric motor or solenoid actuator 130 is connected by linkage arm 133 to damper 132, which moves as indicated in FIG. 11 so as to divert the airstream to an adjacent but interconnecting and parallel duct 135 within which a heater core 134 is mounted. Heater core 134 raises the temperature of the airstream passing through parallel duct 135. Thereafter, heated air is directed toward and onto the face of the surface, thereby raising the temperature of the surface and the ambient space surrounding it so as to preclude condensation, or alternately if condensation is present, vaporizing water droplets deposited thereon.

According to a further option (Option 5), electrical power is supplied by conductor 124 to TEC controller circuit 136, which is electrically grounded by ground 128. TEC controller circuit 136 subsequently energizes TEC 138, through electrical conductors 139 and 140. TEC 138 is positioned relative to duct 129 such that its cold side face directly contacts the exterior surface of, and is mechanically attached, bonded, or otherwise affixed to duct 129. In the same location, heat sink 141 is mechanically attached, bonded or otherwise affixed to the inside surface of duct 129. Heat sink 141 is comprised of a thermally conductive material, which may be constructed with fins, protrusions, or similar extensions, as illustrated. Duct 129 extends past TEC 138 and heat sink 141, thereafter attaching to a 180-degree elbow 144 of the same cross-sectional area and dimensions as duct 129, and positioned within the same plane. Thereafter, elbow 144 attaches to a further duct 143, of the same cross-sectional area and dimensions as duct 129, and is positioned within the same plane as the distal end of elbow 144. Duct 143 extends parallel to duct 129 such that it extends past TEC 138 as illustrated. The hot side of TEC 138 directly contacts the exterior surface of, and is mechanically attached to, bonded to, or otherwise affixed to duct 143. In the same location, heat sink 142 is mechanically attached to, bonded to, or otherwise affixed to the inside surface of duct 143. Heat sink 142 is comprised of a thermally conductive material, which may be constructed with fins, protrusions, or similar extensions, as is illustrated.

In addition to energizing TEC controller 136, switching circuit 120 also concurrently energizes a single-speed or multi-speed fan 125 through conductor 123. Fan 125 is located within duct 129 and is electrically grounded by ground 126. When fan 125 is energized, it rotates or increases its speed in order to generate or increase the volume of airflow directed through duct 129, the airstream flowing past and through TEC cold side heat sink 141, causing moisture in the airstream to be condensed into droplets 145 and to be removed and thereafter past and through TEC hot side heat sink 142, so as to be re-heated and directed toward the surface, thus directing warmed and dehumidified air toward the surface so as to provide condensation suppression action. Water droplets 145 pass to the lower interior surface of elbow 144 in which an opening and drain trap 146 are affixed. Drain trap 146 is constructed with a loop seal so that air passing through duct 129 and elbow 144 are precluded from escaping through trap 146 by the coalesced condensate 147 collected therein. As further moisture droplets 145 are created that then pass to elbow 144 and into trap 146, the increased volume of condensate 147 within trap 146 causes a hydraulic pressure imbalance, resulting in the ejection of condensate, as is illustrated.

A further illustrative embodiment of a condensation detection and suppression system is shown in FIG. 12. Goggles 148 may be intended for underwater use such as by swimmers, but may also be of the type used by construction workers, carpenters, skiers, hazardous materials workers, the military, pilots, etc. Goggles 148 have a transparent faceplate 149, whose inner surface is to be monitored for defogging purposes, and have a circular hole 150 cut out of upper horizontal seal 151. A sensor circuit board 152, positioned in an inverted fashion and containing a humidity sensor and a temperature sensor, is mounted to the underside of a main circuit board 154. The humidity sensor and temperature sensor reside within a protective enclosure 153, which may be fabricated in part out of a hydrophobic material, so as to permit the transference of gases across its boundary but be impermeable to liquid water. Sensor circuit board 152 and protective shroud 153 extend beneath and protrude below the bottom plane of hermetically sealed enclosure 155 such that, when enclosure 155 is affixed to goggles 148 thus mating with upper horizontal seal 151, circuit board 152 and protective shroud 153 insert within hole 150. In such a position, the humidity and temperature sensors (and protective shroud) are placed within the enclosed ambient space formed by the goggles' inner surfaces and the wearer's face.

Main circuit board 154 also contains CPU 156, voltage regulators 157, ADC's 158, and integrated switching mechanism 159. Batteries 160 and 161, positioned within cylindrical recesses 162 and 163, supply direct-current electrical power to main circuit board 154 and sensor circuit board 152. Gasketed threaded end caps 164 and 165 provide hermetic sealing of battery enclosures 162 and 163 respectively.

FIG. 13 illustrates the juxtaposition of the device's ambient-space humidity and thermal sensor with respect to the hydrophobic protective enclosure. Shown rotated along a horizontal axis 180-degrees from that depicted in FIG. 12, humidity sensor 166 and thermal sensor 167 are mounted on common sensor circuit board 168 (corresponding to circuit board 152 of FIG. 12). Protective enclosure 169 (corresponding to protective enclosure 153 of FIG. 12), also shown rotated from its position as depicted in FIG. 12, is of a size and volume sufficient to completely envelop the circuit board 168 and its components. Hydrophobic cover 169 ensures that, should liquid water flood the ambient space (in this case, the space between the inner surface of the goggles and the wearer's face), the device will still work once the water is cleared off of the inner surface of the goggles. Liquid water can still remain in the bottom of the ambient space, but any that splashes or floods the top of the ambient space (where the sensors reside) is prevented by the protective hydrophobic cover from fouling the sensors.

Figure 14:
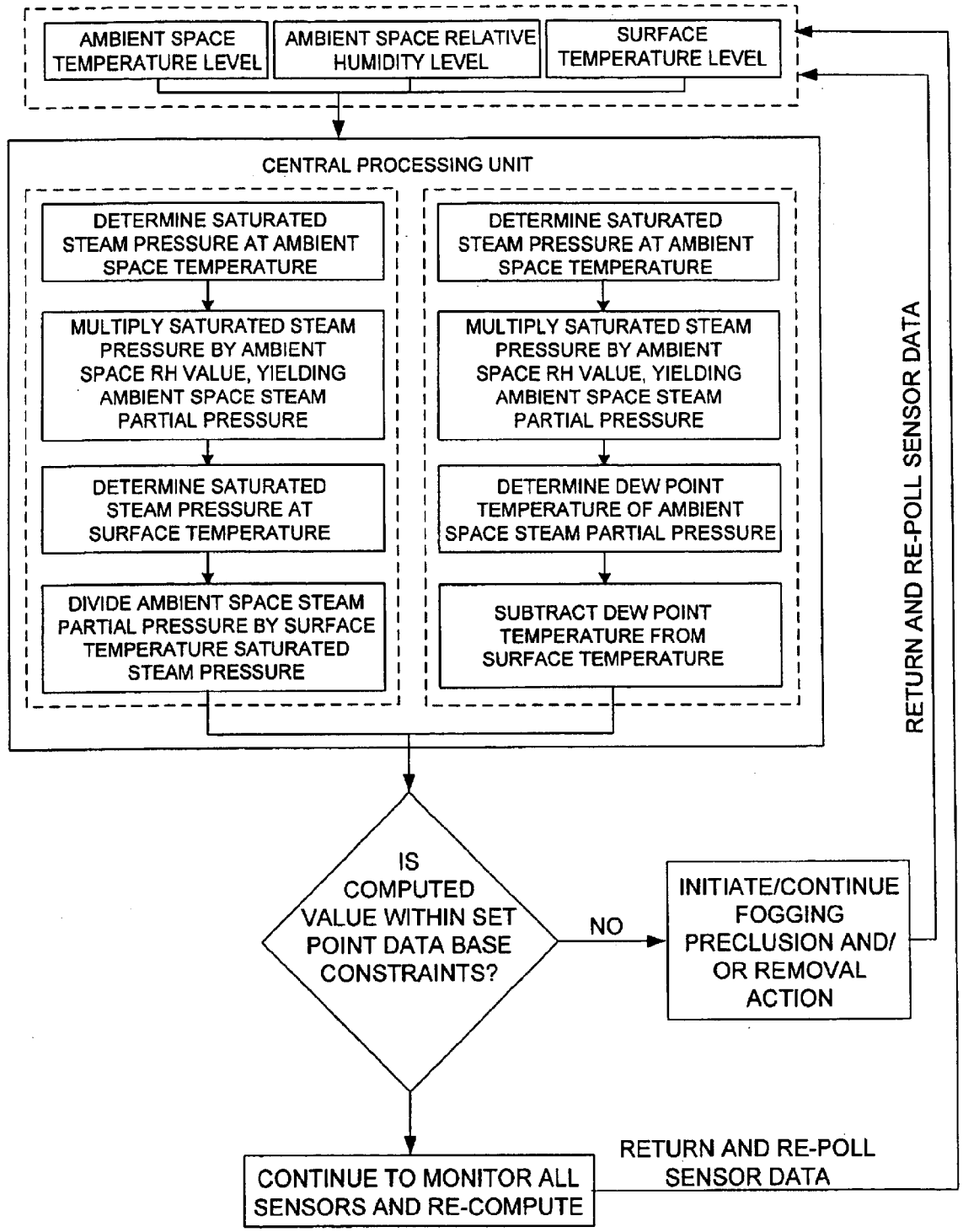
FIG. 14 is a flow diagram of a method for automatically sensing condensation conditions and for suppressing such conditions from a surface using the system illustrated in FIGS. 10 and 11.

With reference to FIG. 14, the ambient space temperature, ambient space relative humidity, and surface temperature levels held in the sample-and-hold buffers are supplied to the central processing unit for analysis according to either of two alternatives as shown. In the first alternative, the CPU computes or determines, through direct calculation (using the Clausius-Clapeyron Equation or any of its derivatives), by accessing an internal look-up table, or by sequentially accessing a look-up table and interpolating or extrapolating and calculation, the theoretical saturated steam pressure in the ambient space at the ambient space temperature. Thereafter, the CPU multiplies this ambient space saturated steam pressure value by the ambient space relative humidity level supplied to it, so as to determine the actual partial pressure of steam in the ambient space. Thereafter, the CPU computes or determines, through direct calculation (using the Clausius-Clapeyron Equation or any of its derivatives), by accessing an internal look-up table, or by sequentially accessing a look-up table and interpolating or extrapolating and calculation, the theoretical saturated steam pressure at the surface temperature previously provided to the CPU. Finally, the CPU compares, by division, the ambient space steam partial pressure to the saturated steam pressure at the surface temperature, to obtain a "pseudo RH" value. This computed value is then compared to the value limit or limits stored in a set-point database. For example, if the value is 1.0 or greater, then condensation either exists on the surface being monitored or is imminent, and defogging action is initiated. If the value is about 0.93 to 1.0, condensation is likely, and preclusive defogging action is initiated. If the value is less than about 0.93, condensation is not likely, and no action is required. Thus, in the event that the computed value is within the bounds or constraints of the database, no action is taken to preclude condensation conditions or remove condensation on the surface. The device then nulls input data values, returns and re-polls the sample and hold buffers and performs a further computational analysis as previously described. In the event that the computed value is outside the bounds or constraints of the database, action is taken to preclude condensation conditions and/or remove condensation on the surface. While this action continues, the device nulls input data values, returns and re-polls the sample and hold buffers, and performs a further computational analysis as described. Condensation preclusion and/or removal action continues until such time that the ratio of the computed ambient space steam partial pressure to the saturated steam at the surface temperature is within the bounds or constraints of the set-point data base.

In a second alternative, the CPU computes or determines, through direct calculation (using the Clausius-Clapeyron Equation or any of its derivatives), by accessing an internal look-up table or by sequentially accessing a look-up table and interpolating or extrapolating and calculation, the theoretical saturated steam pressure in the ambient space at the ambient space temperature provided to the CPU. Thereafter, the CPU multiplies this ambient space saturated steam pressure value by the ambient space relative humidity level supplied to it, so as to determine the actual partial pressure of steam in the ambient space. Thereafter, the CPU computes or determines, through direct calculation (using the Clausius-Clapeyron Equation or any of its derivatives), by accessing an internal look-up table or by sequentially accessing a look-up table and interpolating or extrapolating and calculation, the dew-point temperature of the ambient space steam partial pressure. This value is subtracted from the temperature of the surface, to result in a "pseudo dew point difference" value. Finally, if the CPU-computed value is within the bounds or constraints of the database, no action is taken to preclude condensation conditions or remove condensation on the surface. The device then nulls input data values, returns and re-polls the sample and hold buffers, and performs a further computational analysis as previously described. In the event that the value is outside the bounds or constraints of the database, action is taken to preclude condensation conditions and/or remove condensation on the surface. For example, if the value is greater than about seven, condensation is not likely, and no action is required. If the value is zero or less, then condensation either exists on the surface being monitored or is imminent, and defogging action is initiated. If the value is between zero and about seven, condensation is likely, and preclusive defogging action is initiated. While this action continues, the device nulls input data values, returns and re-polls the sample-and-hold buffers, and performs a further computational analysis as described. Condensation preclusion and/or removal action continues until such time that the difference between the ambient space dew-point temperature and surface temperature is within the bounds or constraints of the set-point database.

There have been described devices and methods for sensing condensation conditions, and for preventing and removing such condensation from surfaces. It will be apparent to those skilled in the art that numerous additions, subtractions, and modifications of the described devices and methods are possible without departing from the spirit and scope of the appended claims. For example, instead of the condensation preclusion and/or removal mechanisms being activated directly by the circuitry disclosed herein, the circuitry could provide a warning to a user of a vehicle that includes the windscreen, the goggles, the helmet that includes the visor, the computer monitor that includes the screen, the room or enclosure that includes the window, the electronic equipment that includes the enclosure, etc., thereby causing the condensation preclusion and/or removal mechanism to be activated by the user.

What is claimed is:

1. A device that determines condensation conditions and suppresses condensation having a given physical state from a surface, comprising:
   a first thermal sensor in thermally conductive contact with the surface;
   a second thermal sensor in an environment separated from the surface;
   a humidity sensor in the environment of the second thermal sensor;
   a condensation suppression mechanism configured to suppress condensation having the given physical state from the surface; and
   a circuit configured to cause the condensation suppression mechanism to be activated when a temperature sensed by the first thermal sensor, a temperature sensed by the second thermal sensor, and a humidity sensed by the humidity sensor indicate that a condensation condition requires suppression at the surface;
   wherein the environment of the second thermal sensor is an ambient space with respect to the surface, and the second thermal sensor is positioned at a sufficient distance from the surface in the ambient space such that the ambient space precludes thermal transfer between the surface and the second thermal sensor.

2. The device of claim 1 wherein the circuit determines that the condensation condition requires suppression at the surface by determining, from the temperature sensed by the second thermal sensor and the humidity sensed by the humidity sensor, the pressure of steam in the environment of the second thermal sensor.

3. The device of claim 2 wherein the circuit determines that the condensation condition requires suppression at the surface by determining a ratio of the pressure of steam in the environment of the second thermal sensor to the saturated steam pressure at the temperature sensed by the first thermal sensor.

4. The device of claim 2 wherein the circuit determines that the condensation condition requires suppression at the surface by determining a difference between a temperature sensed by the first thermal sensor and a dew point temperature associated with the pressure of steam in the environment of the second thermal sensor.

5. The device of claim 1 wherein the condensation condition is a presence of condensation on the surface, and the condensation suppression mechanism is a condensation removal mechanism configured to remove condensation having the given physical state from the surface the device.

6. The device of claim 1 wherein the condensation condition is a near presence of condensation on the surface, and the condensation suppression mechanism is a condensation preclusion mechanism configured to preclude condensation having the given physical state from the surface the device.

7. The device of claim 1 wherein the given physical state is a liquid state.

8. The device of claim 1 wherein the surface is a windscreen.

9. The device of claim 8 wherein the surface is a windscreen of a vehicle.

10. The device of claim 1 wherein the surface is a helmet visor.

11. The device of claim 1 wherein the surface is a computer monitor screen.

12. The device of claim 1 wherein the surface is a window.

13. The device of claim 1 wherein the surface is an enclosure for electronic equipment.

14. The device of claim 1 wherein the surface is an eyewear surface.

15. The device of claim 14 wherein the eyewear surface comprises goggles.

16. The device of claim 15 wherein the goggles are underwater goggles.

17. The device of claim 1 wherein the surface is a respirator mask surface.

18. The device of claim 1 wherein the surface is an optical equipment surface.

19. The device of claim 1 wherein the surface is an electronic circuitry surface.

20. The device of claim 1 wherein the first and second thermal sensors are thermocouples.

21. The device of claim 1 wherein at least one of the first and second thermal sensors is a negative temperature coefficient thermistor.

22. The device of claim 1 wherein the first thermal sensor is in actual physical contact with the surface.

23. The device of claim 1 wherein the first thermal sensor is affixed to the surface.

24. The device of claim 1 wherein the first thermal sensor is embedded within the surface.

25. The device of claim 1 wherein the humidity sensor is a capacitive sensor.

26. The device of claim 1 wherein the condensation suppression mechanism comprises a fan.

27. The device of claim 1 wherein the condensation suppression mechanism comprises a heating mechanism.

28. The device of claim 1 wherein the condensation suppression mechanism comprises a mechanism configured to divert an airstream through a duct having a heating mechanism contained therein.

29. The device of claim 1 wherein the condensation suppression mechanism comprises an infrared source.

30. The device of claim 1 wherein the condensation suppression mechanism comprises a thermoelectric cooler having a cold side that causes moisture in an airstream to be condensed into liquid water and a hot side that subsequently re-heats the airstream.

31. The device of claim 1 wherein the circuit configured to cause the condensation suppression mechanism to be activated is configured to directly activate the condensation suppression mechanism.

32. A device that determines condensation conditions and suppresses condensation having a given physical state from a surface, comprising:
   a first thermal sensor in thermally conductive contact with the surface;
   a second thermal sensor in an environment separated from the surface, the environment being an ambient space with respect to the surface;
   a humidity sensor in the environment of the second thermal sensor;
   a condensation suppression mechanism configured to suppress condensation having the given physical state from the surface;
   a circuit configured to cause the condensation suppression mechanism to be activated when a temperature sensed by the first thermal sensor, a temperature sensed by the second thermal sensor, and a humidity sensed by the humidity sensor indicate that a condensation condition requires suppression at the surface; and
   a protective enclosure enclosing at least the humidity sensor in close proximity to the humidity sensor, the protective enclosure protecting the humidity sensor from exposure to liquid water.

33. The device of claim 32 wherein the protective enclosure further encloses the second thermal sensor and protects the second thermal sensor from exposure to liquid water.

34. The device of claim 32 wherein the protective enclosure is a hydrophobic cover that protects the humidity sensor from exposure to liquid water while permitting transference of gas across its boundary.

35. A method of determining condensation conditions and suppressing condensation having a given physical state from a surface having a first thermal sensor in thermally conductive contact therewith, comprising:

sensing a temperature using the first thermal sensor;

sensing a temperature using a second thermal sensor in an environment separated from the surface;

sensing humidity using a humidity sensor in the environment of the second thermal sensor;

causing a condensation suppression mechanism to be activated in order to suppress condensation having the given physical state from the surface when the temperature sensed by the first thermal sensor, the temperature sensed by the second thermal sensor, and the humidity sensed by the humidity sensor indicate that a condensation condition requires suppression at the surface;

wherein the environment of the second thermal sensor is an ambient space with respect to the surface, and the second thermal sensor is positioned at a sufficient distance from the surface in the ambient space such that the ambient space precludes thermal transfer between the surface and the second thermal sensor.

36. The method of claim 35 wherein the step of causing the condensation suppression mechanism to be activated comprises determining that the condensation condition requires suppression at the surface by determining, from the temperature sensed by the second thermal sensor and the humidity sensed by the humidity sensor, the pressure of steam in the environment of the second thermal sensor.

37. The method of claim 36 wherein the step of determining that the condensation condition requires suppression at the surface comprises determining a ratio of the pressure of steam in the environment of the second thermal sensor to the saturated steam pressure at the temperature sensed by the first thermal sensor.

38. The method of claim 36 wherein the step of determining that the condensation condition requires suppression at the surface comprises determining a difference between a temperature sensed by the first thermal sensor and a dew point temperature associated with the pressure of steam in the environment of the second thermal sensor.

39. The method of claim 35 wherein the condensation condition is a presence of condensation on the surface, and the condensation suppression mechanism is a condensation removal mechanism configured to remove condensation having the given physical state from the surface the device.

40. The method of claim 35 wherein the condensation condition is a near presence of condensation on the surface, and the condensation suppression mechanism is a condensation preclusion mechanism configured to preclude condensation having the given physical state from the surface the device.

41. The method of claim 35 wherein the given physical state is a liquid state.

42. The method of claim 35 wherein the surface is a windscreen.

43. The method of claim 35 wherein the surface is an eyewear surface.

44. The method of claims 43 wherein the eyewear surface comprises goggles.

45. The method of claim 44 wherein the goggles are underwater goggles.

46. The method of claim 44 wherein a protective enclosure encloses at least the humidity sensor, the protective enclosure protecting the humidity sensor from exposure to liquid water.

47. The method of claim 46 wherein the protective enclosure further encloses the second thermal sensor and protects the second thermal sensor from exposure to liquid water.

48. The method of claim 35 wherein the humidity sensor is a capacitive sensor.

* * * * *

UNITED STATES PATENT AND TRADEMARK OFFICE
CERTIFICATE OF CORRECTION

PATENT NO. : 6,834,509 B2
DATED : December 28, 2004
INVENTOR(S) : Valerie Palfy and Don A. Skomsky It is certified that error appears in the above-identified patent and that said Letters Patent is hereby corrected as shown below:

<u>Column 7,</u>
Line 19, replace "necessary-to" with -- necessary to --.

Signed and Sealed this

Seventeenth Day of May, 2005

JON W. DUDAS
*Director of the United States Patent and Trademark Office*